US012611516B2

(12) United States Patent
Zhao et al.

(10) Patent No.: US 12,611,516 B2
(45) Date of Patent: Apr. 28, 2026

(54) TEMPERATURE CONTROL CIRCUIT AND METHOD FOR RESPIRATION TUBE AND RESPIRATION AID EQUIPMENT

(71) Applicants:VINCENT MEDICAL (DONG GUAN) MANUFACTURING CO., LTD, Dongguan (CN); VINCENT MEDICAL (DONG GUAN) TECHNOLOGY CO., LTD, Dongguan (CN)

(72) Inventors: Jun Zhao, Dongguan (CN); Jiebing Xu, Dongguan (CN); Haibin Yu, Dongguan (CN)

(73) Assignees: VINCENT MEDICAL (DONG GUAN) MANUFACTURING CO., LTD, Dongguan (CN); VINCENT MEDICAL (DONG GUAN) TECHNOLOGY CO., LTD, Dongguan (CN)

( * ) Notice: Subject to any disclaimer, the term of this patent is extended or adjusted under 35 U.S.C. 154(b) by 563 days.

(21) Appl. No.: 18/026,992

(22) PCT Filed: Mar. 9, 2022

(86) PCT No.: PCT/CN2022/080036
§ 371 (c)(1),
(2) Date: Mar. 17, 2023

(87) PCT Pub. No.: WO2023/115715
PCT Pub. Date: Jun. 29, 2023

(65) Prior Publication Data
US 2024/0165364 A1      May 23, 2024

(30) Foreign Application Priority Data

Dec. 23, 2021    (CN) .......................... 202111589355.5

(51) Int. Cl.
*A61M 16/10*        (2006.01)
*A61M 16/08*        (2006.01)

(52) U.S. Cl.
CPC .... *A61M 16/1095* (2014.02); *A61M 16/0875* (2013.01); *A61M 2205/14* (2013.01);
(Continued)

(58) Field of Classification Search
CPC .......... A61M 16/0875; A61M 16/1095; A61M 2205/14; A61M 2205/3368; A61M 2205/3653; A61M 2205/6018; F16L 53/38
See application file for complete search history.

(56) References Cited

U.S. PATENT DOCUMENTS

2016/0158480 A1      6/2016  Lim et al.
2018/0200470 A1 *    7/2018  Dixon ............... A61M 16/1095
(Continued)

FOREIGN PATENT DOCUMENTS

CN           102266624 A      12/2011
CN           106994201 A       8/2017
(Continued)

OTHER PUBLICATIONS

Machine translation of CN-108619601-A.*

*Primary Examiner* — Joseph D. Boecker
(74) *Attorney, Agent, or Firm* — MUNCY, GEISSLER, OLDS & LOWE, P.C.

(57) ABSTRACT

A temperature control circuit for a respiration tube is configured to connect to a main board, a power supply end of the main board is connected to a heating wire, and a first
(Continued)

control module connected to the temperature control circuit for the respiration tube is disposed on the main board. The temperature control circuit for the respiration tube includes a detection module and a second control module; the detection module is connected to the second control module and configured to collect a temperature data of the heating wire and transmit the temperature data to the second control module; the second control module is connected to the first control module and the power supply end of the main board. A piece of respiration aid equipment includes the temperature control circuit.

9 Claims, 4 Drawing Sheets

(52) U.S. Cl.
CPC .............. *A61M 2205/3368* (2013.01); *A61M 2205/3653* (2013.01); *A61M 2205/6018* (2013.01)

(56) References Cited

U.S. PATENT DOCUMENTS

| | | | | |
|---|---|---|---|---|
| 2018/0280651 A1 * | 10/2018 | Liu | ................... | A61M 16/0891 |
| 2019/0275281 A1 * | 9/2019 | Creusot | ............. | A61M 16/1095 |
| 2020/0206442 A1 * | 7/2020 | Knepper | ........... | A61M 16/0616 |
| 2024/0131296 A1 * | 4/2024 | Liang | .................. | A61M 16/109 |

FOREIGN PATENT DOCUMENTS

| | | | | | |
|---|---|---|---|---|---|
| CN | 107569753 | A | | 1/2018 | |
| CN | 107802929 | A | | 3/2018 | |
| CN | 108619601 | A | * 10/2018 | ............ A61M 16/16 |
| CN | 108662789 | A | | 10/2018 | |
| CN | 209572168 | U | | 11/2019 | |
| CN | 112295071 | A | | 2/2021 | |
| CN | 112857608 | A | | 5/2021 | |
| WO | WO-2017036500 | A1 | | 3/2017 | |
| WO | WO-2020164120 | A1 | * 8/2020 | ........ A61M 16/1095 |

* cited by examiner

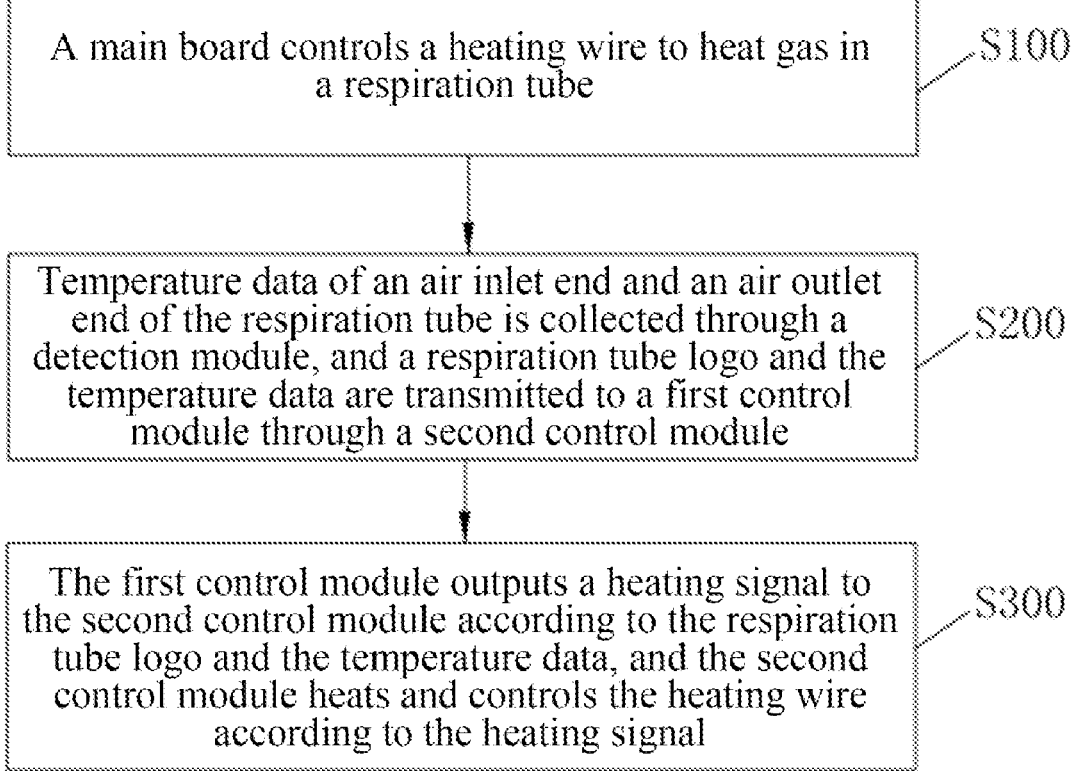

A main board controls a heating wire to heat gas in a respiration tube ⟋S100

Temperature data of an air inlet end and an air outlet end of the respiration tube is collected through a detection module, and a respiration tube logo and the temperature data are transmitted to a first control module through a second control module ⟋S200

The first control module outputs a heating signal to the second control module according to the respiration tube logo and the temperature data, and the second control module heats and controls the heating wire according to the heating signal ⟋S300

FIG. 4

TEMPERATURE CONTROL CIRCUIT AND METHOD FOR RESPIRATION TUBE AND RESPIRATION AID EQUIPMENT

CROSS-REFERENCE TO RELATED APPLICATION

This application is a continuation of International Application No. PCT/CN2022/080036, filed on Mar. 9, 2022, the entire contents of which are incorporated herein by reference.

TECHNICAL FIELD

The present disclosure relates to the technical field of medical devices, in particular to a temperature control circuit and a method for a respiration tube and a piece of respiration aid equipment.

BACKGROUND

The existing respiration aid equipment is usually provided with a variety of pipelines, and each pipeline is provided with an identification element and a temperature detection circuit. The respiration aid equipment identifies pipeline information through the identification element, and temperatures of an air inlet and an air outlet are detected through the temperature detection circuit, and then the respiration working mode is subjected to the corresponding setting.

However, the identification element in the existing respiration aid equipment is connected to a heating wire in the pipeline in series, transmissions of the temperature detection circuit as well as power supply and pipeline signals of the identification element are all completed through a separate line, so that an interface of a main board is occupied more.

Therefore, the prior art still needs to be improved and developed.

SUMMARY

In view of the defects of the prior art, the present disclosure aims at providing a temperature control circuit and a method for a respiration tube and a piece of respiration aid equipment, which can solve the problems that an identification element in the existing respiration aid equipment is connected to a heating wire in a pipeline in series, transmissions of a temperature detection circuit as well as power supply and pipeline signals of the identification element are all completed through a separate line, resulting in an interface of a main board occupied more.

The technical solution of the present disclosure is as follows:

A temperature control circuit for a respiration tube, which is configured to connect to a main board, a power supply end of the main board is connected to a heating wire, a first control module that is connected to the temperature control circuit for the respiration tube is disposed on the main board, and the temperature control circuit for the respiration tube includes a detection module and a second control module;

the detection module is connected to the second control module, and the detection module is configured to collect temperature data of the heating wire and to transmit the temperature data to the second control module;

the second control module is connected to the first control module and the power supply end of the main board, and the second control module is configured to transmit a respiration tube logo and the temperature data to the first control module;

the first control module outputs a heating signal to the second control module according to the respiration tube logo and the temperature data, and the second control module heats and controls the heating wire according to the heating signal.

In the above technical solution, the present disclosure implements the collection and transmission for the respiration tube logo and the temperature data as well as the transmission of the heating signal through the first control module and the second control module, and the heating wire and the second control module may share the power supply end of the main board, or the second control module, the power supply of the heating wire and the communication between the first control module and the second control module all share the power supply end of the main board, thus the use of the line may be reduced, thereby reducing the interface occupation of the main board.

According to the further setting of the present disclosure, the second control module is connected to the power supply end of the main board, and connected to the first control module through the power supply end; after the first control module modulates the heating signal, a first modulation signal is obtained and sent to the second control module, the second control module demodulates the first modulation signal so as to obtain a first demodulation signal for heating and controlling the heating wire, and the respiration tube logo and the temperature data are modulated to obtain a second modulation signal and the second modulation signal is transmitted to the first control module; and the first control module demodulates the second modulation signal so as to obtain a second demodulation signal.

According to the further setting of the present disclosure, the first control module includes a first control chip, on which a signal emission pin and a signal receiving pin are disposed; and the second control module includes a second control chip, on which a signal emission pin, a signal receiving pin, a power pin and a heating control pin are disposed;

the signal emission pin of the second control chip is connected to the signal receiving pin of the first control chip;

the signal receiving pin of the second control chip is connected to the signal emission pin of the first control chip;

the power pin of the second control chip is connected to the power supply end of the main board; and the heating control pin of the second control chip is configured to control the disconnection or connection between the power supply end of the main board and the heating wire.

According to the further setting of the present disclosure, the first control module includes the first control chip, on which a signal receiving and sending pin is disposed; and the second control module includes the second control chip, on which a signal receiving and sending pin, a power pin and a heating control pin are disposed;

the signal receiving and sending pin of the second control chip is connected to the signal receiving and sending pin of the first control chip;

the power pin of the second control chip is connected to the power supply end of the main board;

the heating control pin of the second control chip is configured to control the disconnection or connection between the power supply end of the main board and the heating wire.

According to the further setting of the present disclosure, the temperature control circuit for the respiration tube further includes a first voltage conversion unit, an input end of the first voltage conversion unit is connected to the power supply end of the main board, and an output end of the first voltage conversion unit is connected to the power pin of the second control chip.

According to the further setting of the present disclosure, the temperature control circuit for the respiration tube further includes a first switch, which is connected between the power supply end of the main board and the heating wire, and connected to the heating control pin of the second control chip.

According to the further setting of the present disclosure, the detection module includes a first temperature sensor and a second temperature sensor;

one end of the first temperature sensor is connected to a first power supply pin of the second control chip, and the other end of the first temperature sensor is connected to a grounding pin of the main board;

one end of the second temperature sensor is connected to a second power supply pin of the second control chip, and the other end of the second temperature sensor is connected to the grounding pin of the main board;

According to the further setting of the present disclosure, the first temperature sensor and the second temperature sensor are all thermistors Based on the same inventive concept, the present disclosure further provides a temperature control method for a respiration tube, and the method applies the above temperature control circuit for the respiration tube and includes the following steps:

a main board controls a heating wire to heat gas in the respiration tube;

temperature data of an air inlet end and an air outlet end of the respiration tube is collected through a detection module, and a respiration tube logo and the temperature data are transmitted to a first control module through a second control module;

the first control module outputs a heating signal to the second control module according to the respiration tube logo and the temperature data, and the second control module heats and controls the heating wire according to the heating signal.

Based on the same inventive concept, the present disclosure further provides a piece respiration aid equipment, including a main board and the above temperature control circuit for the respiration tube; and a power supply end of the main board is connected to a heating wire, and a first control module connected to the temperature control circuit for the respiration tube is disposed on the main board.

BRIEF DESCRIPTION OF THE DRAWINGS

To better clarify the embodiment of the present disclosure or the technical solution in the prior art, the drawings required to illustrate the embodiments or the prior art will be simply described below. It is apparent that the drawings described below merely illustrate some embodiments of the present disclosure. Those ordinarily skilled in the art can obtain other drawings according to the structures of these drawings without creative labor on the basis of those drawings.

FIG. 4 is a flow diagram for a temperature control method for a respiration tube in one embodiment of the present disclosure.

Reference signs: 100—main board, 200—first control module, 300—detection module, 400—second control module.

DETAILED DESCRIPTION OF THE EMBODIMENTS

The present disclosure provides a temperature control circuit and a method for a respiration tube and a piece of respiration aid equipment. In order to make the objectives, technical solution and effects of the present disclosure clearer and definer, the examples of the present disclosure will be described in detail below in conjunction with the drawings. It is understood that the specific embodiments described herein are merely used for explaining the present disclosure, instead of limiting the present disclosure.

In the scope of the implementation mode and the applied patent, "a/an", "one", and "the" and "this" may include the plural forms, unless otherwise specified in the context. If the descriptions "first" and "second" are involved in the embodiments of the present disclosure, the descriptions "first" and "second" are merely used for description, instead of being understood as indicating or implying relative importance or impliedly indicating the quantity of the showed technical features. Thus, the features defined with "first" and "second" may expressly or impliedly one or more features.

It is further understood that term"include" used in the specification of the present disclosure means the feature, integer, step, operation, unit and/or component, but not excluding existing or added one or a plurality of features, integers, steps, operations, units and/or components and/or their combination. It is understood that when the unit is "connected" or "coupled" to another unit, it may be directly connected or coupled to other units, or there may be an intermediate unit. In addition, "connecting" or "coupling" used here may include wireless connection or wireless coupling. Terms "and/or" used here include all of one or more associated list items or any unit or all combinations.

Those skilled in the art may understood, unless otherwise defined, all terms (including technical terms and scientific terms) used here have the same meaning as the general understanding of those of ordinary skill in the art. It is also understood that, for example, those terms defined in a general dictionary shall be understood as the same meaning consistent with that in the text of the prior art, and unless being specifically defined herein, otherwise, it cannot be explained in an ideal or formal meaning.

Thus, the technical solutions of various embodiments may be mutually combined, but must be achieved by those of ordinary skill in the art. When the combination of the technical solution has mutual contradiction or cannot be achieved, it should believe that such combination of the technical solution does not exist and does not fall in the protection range required by the present disclosure.

Figure 1:
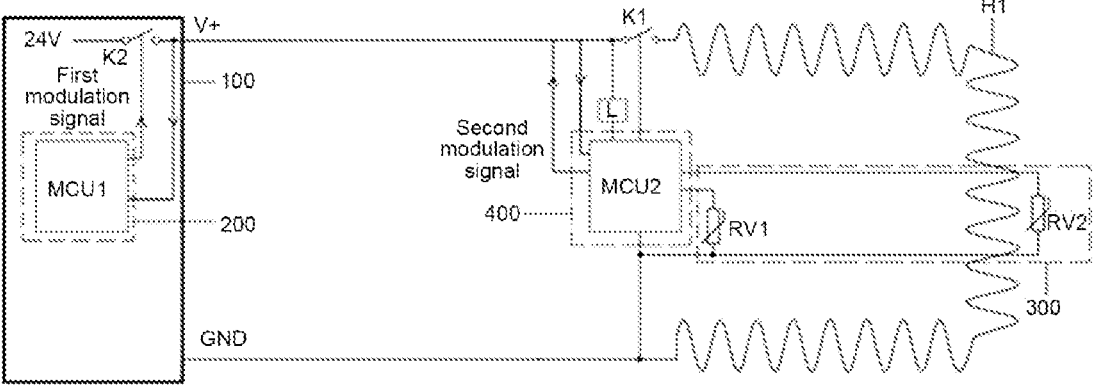
FIG. 1 is a schematic diagram for connecting a temperature control circuit for a respiration tube with a main board in one embodiment of the present disclosure.
Figure 2:
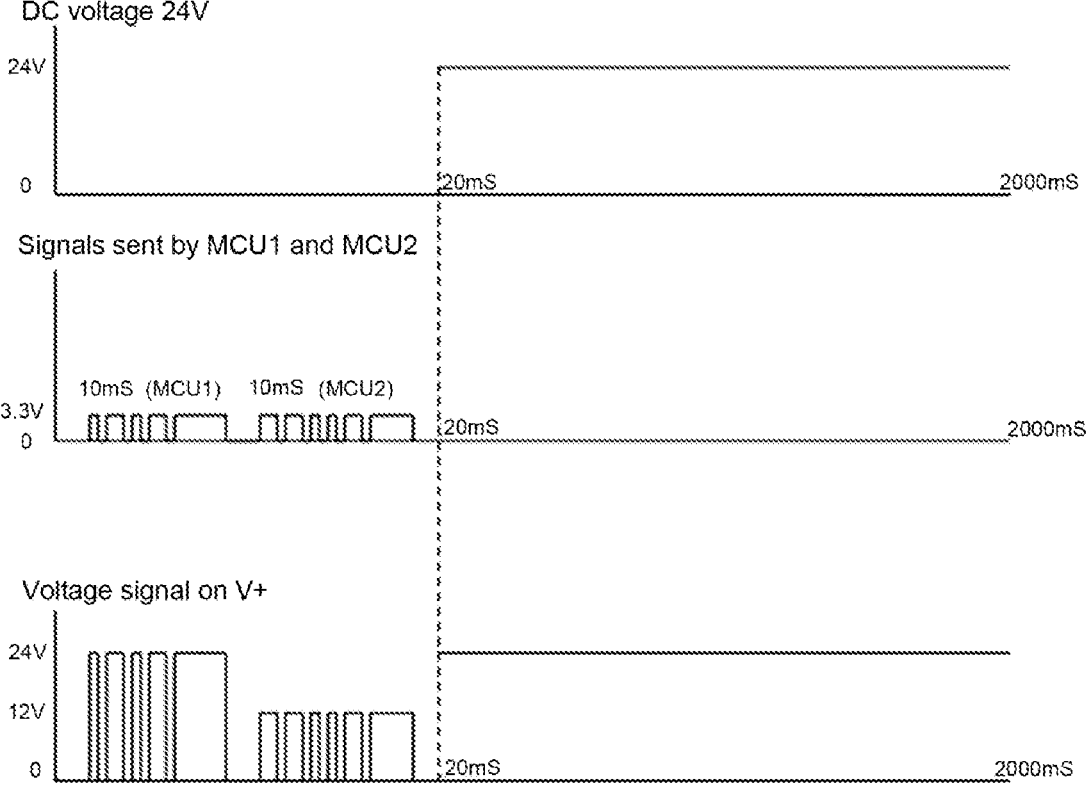
FIG. 2 is a a signal modulation schematic diagram for MCU1 and MCU2 signal transmission.
Figure 3:
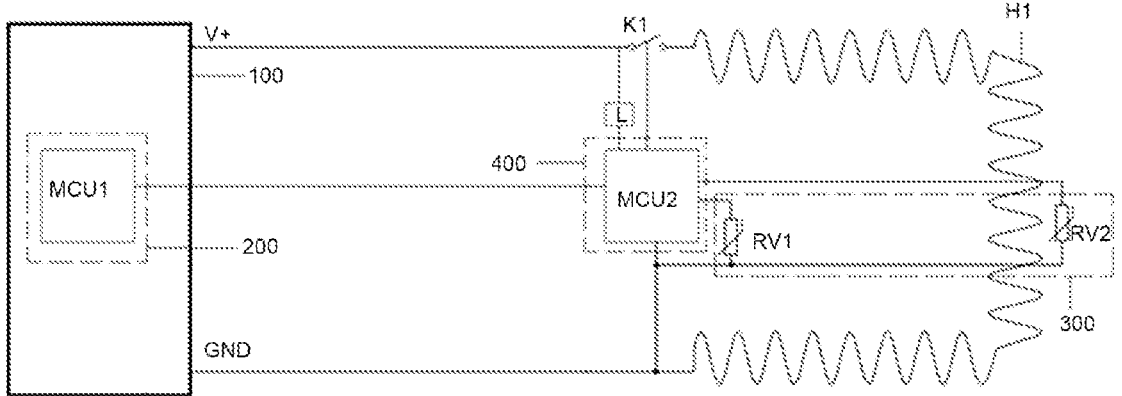
FIG. 3 is a schematic diagram for connecting a temperature control circuit of a respiration tube with a main board in another embodiment of the present disclosure.

Please refer to FIG. 1 to FIG. 3 at the same time, the present disclosure provides a preferred embodiment of a temperature control circuit for a respiration tube.

As shown in FIG. 1 and FIG. 3, the present disclosure provides a temperature control circuit for a respiration tube, which is configured to connect to a main board 100, a power supply end of the main board 100 is connected to a heating wire H1, a first control module 200 that is connected to the temperature control circuit for the respiration tube is disposed on the main board 100, and the temperature control circuit for the respiration tube includes a detection module 300 and a second control module 400. The detection module 300 is connected to the second control module 400 and configured to collect temperature data of the heating wire H1 and transmit the temperature data to the second control module 400; the second control module 400 is connected to the first control module 200 and the power supply end of the main board 100, and the second control module 400 is configured to transmit a respiration tube logo and the temperature data to the first control module 200. The first control module 200 outputs a heating signal to the second control module 400 according to the respiration tube logo and the temperature data, and the second control module 400 heats and controls the heating wire H1 according to the heating signal.

In the above technical solution, the present disclosure implements the collection and transmission for the respiration tube logo and the temperature data as well as the transmission of the heating signal through the first control module 200 and the second control module 400, and the heating wire H1 and the second control module 400 may share the power supply end of the main board 100, or the second control module 400, the power supply of the heating wire H1 and the communication between the first control module 200 and the second control module 400 all share the power supply end of the main board 100, thus the use of the line may be reduced, thereby reducing the interface occupation of the main board 100.

As shown in FIG. 1, in some embodiments, the second control module 400 is connected to the power supply end V+ of the main board 100, and connected to the first control module 200 through the power supply end V+; after the first control module 200 modulates the heating signal, a first modulation signal is obtained and sent to the second control module 400, the second control module 400 demodulates the first modulation signal so as to obtain a first demodulation signal for heating and controlling the heating wire H1, and the respiration tube logo and the temperature data are modulated to obtain a second modulation signal and the second modulation signal is transmitted to the first control module 200; and the first control module 200 demodulates the second modulation signal so as to obtain a second demodulation signal, and the first control module 200 outputs the heating signal to the second control module 400 according to the second demodulation signal.

Specifically, the first control module 200 includes a first control chip MCU1, on which a signal emission pin and a signal receiving pin are disposed. The second control module 400 includes a second control chip MCU2, on which a signal emission pin, a signal receiving pin, a power pin and a heating control pin are disposed. The signal emission pin of the second control chip MCU2 is connected to the signal receiving pin of the first control chip MCU1, the signal receiving pin of the second control chip MCU2 is connected to the signal emission pin of the first control chip MCU1, the power pin of the second control chip MCU2 is connected to the power supply end V+ of the main board 100, and the heating control pin of the second control chip MCU2 is configured to control the disconnection or connection between the power supply end V+ of the main board 100 and the heating wire H1.

The signal emission pin of the second control chip MCU2 is connected to the signal receiving pin of the first control chip MCU1 through the power supply end V+ on the main board 100, the signal receiving pin of the second control chip MCU2 is connected to the signal emission pin of the first control chip MCU1 through the power supply end V+ of the main board 100.

A second switch K2 is also disposed on the main board 100, one end of the second switch K2 is connected to a 24V power supply, and the other end of the second switch K2 is connected to the power supply end V+ of the main board 100. When the first control chip MCU1 sends out the first modulation signal to the second control chip MCU2, the second switch K2 is closed; and when the first control chip MCU1 receives the second modulation signal sent by the second control chip MCU2, namely, when the second modulation signal is demodulated to obtain the second modulation signal, the second switch K2 is disconnected.

Further, the temperature control circuit for the respiration tube further includes a first voltage conversion unit, an input end of the first voltage conversion unit is connected to the power supply end V+ of the main board 100, and an output end of the first voltage conversion unit is connected to the power pin of the second control module 400.

Specifically, the first voltage conversion unit is a voltage conversion chip L, which is connected between the power pin of the second control chip MCU2 and the power supply end V+ of the main board 100 so as to convert the 24 V voltage output by the main board 100 into a 3.3 V power supply voltage required by the second control chip MCU2. When the first control chip MCU1 sends the first modulation signal to the second control chip MCU2, the first modulation signal is the 3.3 V DC current signal. When the second control chip MCU2 sends the second modulation signal to the first control chip MCU1, the second modulation signal is the 3.3 V DC current signal.

In combination with FIG. 2, take a control period with 2,000 ms as an example, at the first 10 ms every 2,000 ms, the first control chip MCU1 sends a heating signal and a related acquired command, and the first control chip MCU1 loads the signal required to be sent on a 24 V DC voltage. The related command is sent in the first 10 ms, namely, the first modulation signal is sent, and the second modulation signal sent back by the second control chip MCU2 in the second 10 ms section is demodulated so as to obtain the second demodulation signal. In the second 10 ms, the second control chip MCU2 sends and collects the respiration tube logo (the second control chip MCU2 may collect the respiration tube logo of the respiration tube or store the respiration tube logo directly) and the temperature data, the signal required to be sent is loaded on the 12 V DC voltage, namely, the second demodulation signal is sent. The related command is sent in the second 10 ms, the first modulation signal sent by the first control chip MCU1 is demodulated in the first 10 ms so as to obtain the first demodulation signal, and the second control chip MCU2 heats and controls the heating wire H1 according to the first demodulation signal.

It is understood that 20 ms only accounts for 1% of 2,000 ms, therefore the influence on the maximum heating power of the heating wire H1 in a heating circuit may be ignored. Of course, the signal transmission control period between the first control chip MCU1 and the second control chip MCU2 is also not limited as 2,000 ms.

Referring to FIG. 1, further, the temperature control circuit for the respiration tube further includes a first switch K1, which is connected between the power supply end V+ of the main board 100 and the heating wire H1, and connected to the heating control pin of the second control chip MCU2.

Specifically, when the second control chip MCU2 receives the first modulation signal sent by the first control chip MCU1 and obtains the first demodulation signal, the disconnection or connection of the first switch K1 is controlled according to the first demodulation signal, namely, whether to heat the heating wire H1 is controlled.

It is noted that the transmission data between the first control chip MCU1 and the second control chip MCU2 includes but is not limited to a request command, respiration tube logo data, temperature data or a checksum, and the transmission data is a group of two-stage system data. The respiration tube logo data may include a loop identification code, a respiration tube type, a respiration tube model, etc.

Referring to FIG. 1, in a further implementation mode of one embodiment, the detection module 300 includes a first temperature sensor RV1 and a second temperature sensor RV2. One end of the first temperature sensor RV1 is connected to a first power supply pin of the second control chip MCU2, and the other end of the first temperature sensor RV1 is connected to a grounding pin of the main board 100; one end of the second temperature sensor RV2 is connected to a second power supply pin of the second control chip MCU2, and the other end of the second temperature sensor RV2 is connected to a grounding pin of the main board 100.

Specifically, the first temperature sensor RV1 is located at an air inlet of the respiration tube, so as to detect the temperature data at the air inlet of the respiration tube. The second temperature sensor RV2 is located at an air outlet of the respiration tube, so as to detect the temperature at the air outlet of the respiration tube. The second control chip MCU2 supplies power to the first temperature sensor RV1 and the second temperature sensor RV2, and the first temperature sensor RV1 and the second temperature sensor RV2 can feed the detected temperature data back to the second control chip MCU2. In one implementation mode, the first temperature sensor RV1 and the second temperature sensor RV2 may be thermistors.

In the above embodiment, the power supply of the second control chip MCU2 and the heating wire H1 are all connected to the power supply end V+ of the main board 100, and the first control chip MCU1 is also connected to the second control chip MCU2 through the power supply end V+, then the communication between the first control chip MCU1 and the second control chip MCU2 may be implemented by a single wire only. The other end of the heating wire H1 is connected to the grounding end GND of the main board 100, so the connection between the temperature control circuit for the respiration tube and the main board 100 may be implemented by two wires only, thereby greatly reducing the interface occupation of the main board 100.

As shown in FIG. 3, in another embodiment, the first control module 200 includes the first control chip MCU1, on which a signal receiving and sending pin is disposed; and the second control module 400 includes the second control chip MCU2, on which a signal receiving and sending pin, a power pin and a heating control pin are disposed. The signal receiving and sending pin of the second control chip MCU2 is connected to the signal receiving and sending pin of the first control chip MCU1, the power pin of the second control chip MCU2 is connected to the power supply end V+ of the main board 100, and the heating control pin of the second control chip MCU2 is configured to control the disconnection or connection between the power supply end V+ of the main board 100 and the heating wire H1.

Specifically, the second control chip MCU2 and the heating wire H1 are connected to the power supply end V+ of the main board 100 through one line, the other end of the heating wire H1 is connected to the grounding end GND of the main board 100, the communication between the first control chip MCU1 and the second control chip MCU2 is completed through a single circuit, namely, the transmission of the heating signal, the respiration tube logo and the temperature data is implemented. The power pin of the second control chip MCU2 is connected to a first voltage conversion chip L, so as to implement the conversion of the 24 V DC current output by the main board 100 into the power supply voltage 3.3 V of the second control chip MCU2. Similarly, the first switch K1 is also disposed between the heating wire H1 and the power supply end V+ of the main board 100, the first switch K1 is connected to the heating control pin of the second control chip MCU2, and the first switch K1 is controlled to be turned on or turned off through the heating control pin, thereby controlling the heating of the heating wire H1.

In the above embodiment, the power supply of the heating wire H1 and the second control chip MCU2 is connected to the main board 100 through one line, the line that the temperature data collected by the first temperature sensor RV1 and the second temperature sensor RV2 and the respiration tube logo of the respiration tube are sent to the first control chip MCU1 through the second control chip MCU2 is the same as the line that the heating signal of the first control chip MCU1 is sent to the second control chip MCU2, thus the temperature control circuit for the respiration tube only requires three lines to implement the connection with the main board 100, thereby greatly reducing the interface occupation of the main board 100.

Referring to FIG. 4, in some embodiments, the present disclosure further provides a temperature control method for a respiration tube, and the method applies the above temperature control circuit for the respiration tube and includes the following steps:

S100: a main board controls a heating wire to heat gas in the respiration tube;

S200: temperature data of an air inlet end and an air outlet end of the respiration tube is collected through a detection module, and a respiration tube logo and the temperature data are transmitted to a first control module through a second control module; and S300: the first control module outputs a heating signal to the second control module according to the respiration tube logo and the temperature data, and the second control module heats and controls the heating wire according to the heating signal. Specifically, the method is as the description of the embodiment for the temperature control method for the respiration tube, so repetition is not made herein.

In some embodiments, the present disclosure further provides a piece of respiration aid equipment, which may be a respirator, etc. The equipment includes a plurality of respiration tubes, on which the heating wire is wound. The respiration aid equipment further includes a main board and the above temperature control circuit for the respiration tube; and a power supply end of the main board is connected to a heating wire, and a first control module connected to the temperature control circuit for the respiration tube is disposed on the main board. The temperature control method for the respiration tube is specifically as the description for the temperature control circuit of the respiration tube, so repetition is not made herein.

It is understood that the application of the present disclosure is not limited to the above examples, those of ordinary skill in the art can make improvements or changes according to the above specification. However, these improvements or changes fall in the protection scope of the claims of the present disclosure.

What is claimed is:

1. A temperature control circuit for a respiration tube, connected to a main board, a power supply end of the main board is connected to a heating wire, a first control module included in the temperature control circuit is disposed on the main board, wherein the temperature control circuit for the respiration tube comprises a detection module and a second control module;

the detection module is connected to the second control module, and the detection module is configured to collect temperature data of the heating wire and to transmit the temperature data to the second control module;

the second control module is connected to the first control module and the power supply end of the main board, and the second control module is configured to transmit a respiration tube identifier and the temperature data to the first control module; and the first control module outputs a heating signal to the second control module according to the respiration tube identifier and the temperature data, and the second control module heats and controls the heating wire according to the heating signal.

2. The temperature control circuit for the respiration tube according to claim 1, wherein the second control module is connected to the first control module through the power supply end; after the first control module modulates the heating signal, a first modulation signal is obtained and sent to the second control module, the second control module demodulates the first modulation signal so as to obtain a first demodulation signal for heating and controlling the heating wire, and the respiration tube identifier and the temperature data are modulated to obtain a second modulation signal and the second modulation signal is transmitted to the first control module; and the first control module demodulates the second modulation signal so as to obtain a second demodulation signal.

3. The temperature control circuit for the respiration tube according to claim 2, wherein the first control module comprises a first control chip, on which a signal emission pin and a signal receiving pin are disposed; and the second control module comprises a second control chip, on which a signal emission pin, a signal receiving pin, a power pin and a heating control pin are disposed;

the signal emission pin of the second control chip is connected to the signal receiving pin of the first control chip;

the signal receiving pin of the second control chip is connected to the signal emission pin of the first control chip;

the power pin of the second control chip is connected to the power supply end of the main board; and the heating control pin of the second control chip is configured to control a disconnection or connection between the power supply end of the main board and the heating wire.

4. The temperature control circuit for the respiration tube according to claim 3, wherein the temperature control circuit for the respiration tube further comprises a first voltage conversion unit, an input end of the first voltage conversion unit is connected to the power supply end of the main board, and an output end of the first voltage conversion unit is connected to the power pin of the second control chip.

5. The temperature control circuit for the respiration tube according to claim 3, wherein the temperature control circuit for the respiration tube further comprises a first switch, which is connected between the power supply end of the main board and the heating wire, and connected to the heating control pin of the second control chip.

6. The temperature control circuit for the respiration tube according to claim 3, wherein the detection module comprises a first temperature sensor and a second temperature sensor;

one end of the first temperature sensor is connected to a first power supply pin of the second control chip, and another end of the first temperature sensor is connected to a grounding pin of the main board; and one end of the second temperature sensor is connected to a second power supply pin of the second control chip, and another end of the second temperature sensor is connected to the grounding pin of the main board.

7. The temperature control circuit for the respiration tube according to claim 6, wherein the first temperature sensor and the second temperature sensor are all thermistors.

8. The temperature control circuit for the respiration tube according to claim 1, wherein the first control module comprises a first control chip, on which a signal receiving and sending pin is disposed; and the second control module comprises a second control chip, on which a signal receiving and sending pin, a power pin and a heating control pin are disposed;

the signal receiving and sending pin of the second control chip is connected to the signal receiving and sending pin of the first control chip;

the power pin of the second control chip is connected to the power supply end of the main board; and the heating control pin of the second control chip is configured to control a disconnection or connection between the power supply end of the main board and the heating wire.

9. A temperature control method for a respiration tube, and the method applies the temperature control circuit for the respiration tube according to claim 1, and the method comprises the following steps:

the main board controls the heating wire to heat gas in the respiration tube;

temperature data of an air inlet end and an air outlet end of the respiration tube is collected through the detection module, and the respiration tube identifier and the temperature data are transmitted to the first control module through the second control module; and the first control module outputs the heating signal to the second control module according to the respiration tube identifier and the temperature data, and the second control module heats and controls the heating wire according to the heating signal.

* * * * *